US009937245B2

United States Patent
Pfeil et al.

(10) Patent No.: US 9,937,245 B2
(45) Date of Patent: Apr. 10, 2018

(54) HIGHLY PURE NEUROTOXIC COMPONENT OF A BOTULINUM TOXIN, PROCESS FOR PREPARING SAME, AND USES THEREOF

(71) Applicant: MERZ PHARMA GMBH & CO. KGAA, Frankfurt am Main (DE)

(72) Inventors: Michael Pfeil, Koenigstein im Taunus (DE); Andreas Wiesenburg, Jena (DE)

(73) Assignee: MERZ PHARMA GMBH & CO. KGAA, Frankfurt am Main (DE)

( * ) Notice: Subject to any disclaimer, the term of this patent is extended or adjusted under 35 U.S.C. 154(b) by 0 days.

(21) Appl. No.: 14/908,235

(22) PCT Filed: Jul. 30, 2014

(86) PCT No.: PCT/EP2014/002089
§ 371 (c)(1),
(2) Date: Jan. 28, 2016

(87) PCT Pub. No.: WO2015/014487
PCT Pub. Date: Feb. 5, 2015

(65) Prior Publication Data
US 2016/0175407 A1 Jun. 23, 2016

(30) Foreign Application Priority Data
Jul. 30, 2013 (EP) .................................... 13003792

(51) Int. Cl.
| | |
|---|---|
| A61K 39/08 | (2006.01) |
| A61K 38/48 | (2006.01) |
| C07K 14/33 | (2006.01) |
| C12M 1/12 | (2006.01) |
| C12M 1/34 | (2006.01) |
| C12N 1/20 | (2006.01) |
| C12N 9/52 | (2006.01) |

(52) U.S. Cl.
CPC .......... *A61K 38/4893* (2013.01); *A61K 39/08* (2013.01); *C07K 14/33* (2013.01); *C12M 37/00* (2013.01); *C12M 41/40* (2013.01); *C12N 1/20* (2013.01); *C12N 9/52* (2013.01); *C12Y 304/24069* (2013.01)

(58) Field of Classification Search
None
See application file for complete search history.

(56) References Cited

U.S. PATENT DOCUMENTS

| | | | | |
|---|---|---|---|---|
| 9,469,849 | B2 * | 10/2016 | Ruegg ............ | C12Y 304/24069 |
| 2005/0254055 | A1 * | 11/2005 | Peng ...................... | C12M 41/36 356/432 |
| 2008/0187967 | A1 * | 8/2008 | Doelle ................... | C12M 37/02 435/71.3 |
| 2012/0088732 | A1 * | 4/2012 | Bigalke .............. | C07K 16/1282 514/17.7 |
| 2012/0189677 | A1 * | 7/2012 | Tonge ...................... | A61K 9/06 424/401 |

OTHER PUBLICATIONS

Fang P. et al. Analysis of Genomic Differences Among Clostridium botulinum Type A 1 Strains. BMC Genomics 11:725, pp. 1-8, Dec. 2010.*
Siegel L. et al. Toxin Production by C. botulinum Type A Under Various Fermentation Conditions. Applied and Environmental Microbiology 38(4)606-611, 1979.*
Lacy D. et al. Crystal Structure of B. Neurotoxin Type A and Implications for Toxicity. Nature Structural Biology 5(10)898-902, Oct. 1998.*
DasGupta B. et al. Purification and Amino Acid Composition of Type A B. Neurotoxin. Toxicon 22(3)415-424, 1984.*
Waters T. The Fine Art of Making Poison. Discover Magazine Aug. 1992, 1-6.*
Montville T. Interaction of pH and NaCl on Culture Density of C. botulinum 62A. Applied and Environmental Micro 46(4)961-963, Oct. 1983.*
Sharkey F. et al. Quantification of Toxin Encoding mRNA from C. botulinum Type E in Media Containing . . . FEMS Microbiology 232:139-144, Feb. 2004.*
International Search Report from corresponding PCT/EP2014/002089, dated Oct. 13, 2014.
Borden et al., "Crystal structure of botulinum neurotoxin type A and implications for toxicity" Natural Structural Biology. (Oct. 1998) vol. 5, No. 10: 898-902.

* cited by examiner

*Primary Examiner* — Ralph J Gitomer
(74) *Attorney, Agent, or Firm* — McBee Moore Woodward & Vanik IP, LLC

(57) ABSTRACT

The present invention relates to a process for preparing a highly pure neurotoxic component of a *botulinum* toxin by cultivating *clostridium botulinum* under conditions that allow production of a *botulinum* toxin, and isolating the neurotoxic component from the *botulinum* toxin. In addition, the present invention relates to a highly pure neurotoxic component of a *botulinum* toxin obtainable by the process of the present invention and uses thereof.

20 Claims, No Drawings

HIGHLY PURE NEUROTOXIC COMPONENT OF A BOTULINUM TOXIN, PROCESS FOR PREPARING SAME, AND USES THEREOF

CROSS REFERENCE TO RELATED APPLICATIONS

This application is a § 371 National Stage Application of PCT International Application Number PCT/EP2014/00289 filed on 30 Jul. 2014 which claims priority to EP 13 003 792.2 filed 30 Jul. 2013.

BACKGROUND

Field of the Invention

The present invention relates to a process for preparing a highly pure neurotoxic component of a *botulinum* toxin by cultivating *Clostridium botulinum* under conditions that allow production of a *botulinum* toxin, and isolating the neurotoxic component from the *botulinum* toxin. In addition, the present invention relates to a highly pure neurotoxic component of a *botulinum* toxin obtainable by the process of the present invention and uses thereof.

Description of Related Art

*Botulinum* toxins are the most potent protein toxins for humans. They act by blocking acetylcholine release at the neuromuscular junction resulting in denervation of muscles. *Botulinum* toxins also have activity at other peripheral cholinergic nerve terminals and lead, for example, to reduced salivation or sweating and to diminished facial lines and wrinkles. Due to their specificity of mode of action, the range of clinical applications of *botulinum* toxins is continuously growing, and *botulinum* toxins are today being used extensively as pharmaco-cosmetics.

The *botulinum* toxins are synthesized and released by certain *Clostridium* spp. in the form of large complexes comprising the *botulinum* toxin molecule (the "neurotoxic component") and associated non-toxic bacterial proteins (also referred to as "complexing proteins"). The complexing proteins include different non-toxic hemagglutinin (HA) proteins and non-toxic non-hemagglutinin (NTNH) proteins. The molecular weight of the toxin complex varies among the seven distinct *botulinum* toxin serotypes (A, B, C, D, E, F and G) from about 300 kDa to about 900 kDa. The complexing proteins provide stability to the neurotoxic component. Unlike the toxin complex, the neurotoxic component in its isolated and pure form, i.e. devoid of any complexing clostridial proteins, is acid labile and does not resist the aggressive environment in the gastrointestinal tract.

The neurotoxic component is synthesized as an inactive single-chain precursor (non-cleaved polypeptide) having a molecular weight, for all seven of the known *botulinum* toxin serotypes, of about 150 kDa. This single-chain precursor is activated by proteolytic cleavage to generate a disulfide-linked two-chain protein. The 50 kDa light chain contains the catalytic domain, whereas the 100 kDa heavy chain contains an internal translocation domain and a receptor binding domain. The 100 kDa heavy chain mediates binding to pre-synaptic cholinergic nerve terminals and internalization of the toxin into the cell. The 50 kDa light chain is responsible for the toxic effects, acting as zinc-endopeptidase and cleaving specific proteins responsible for membrane fusion (proteins of the SNARE complex). By disrupting the process of membrane fusion within the nerve cells, *botulinum* toxins prevent the release of acetylcholine into the synaptic cleft.

The *botulinum* toxin serotype A complex (BoNT/A-complex) was first approved for human use in the United States in 1989 for the treatment of strabism, blepharospasm, and other disorders. Today, the "A" form of the *botulinum* toxin complex is available commercially from several sources, for example from Allergan under the trade name Botox®, from Ipsen under the trade name Dysport®, and from Galderma under the trade name Azzalure®.

However, in a significant number of cases, patients produced neutralizing antibodies in response to repeated BoNT/A-complex injections. It is believed that this effect is associated with the complexing proteins of the BoNT/A-complex. The patients affected become so-called "secondary non-responders", and therapy with the BoNT/A-complex is no longer effective. This risk for such antibody-induced therapy failure was found to affect no less than 10% to 20% of the subjects treated. Another disadvantage associated with the use of the *botulinum* toxin complex is its regional or systemic spread following injections into the target muscles. For example, studies using single-fibre electromyography (SF-EMG) have shown increased jitter in muscles distant from the injection site.

These disadvantages are not observed with the administration of the pure neurotoxic component. In particular, administration of the pure neurotoxic component reduces the risk of non- or decreased response, which is of particular importance for patients undergoing long-term treatments. Other benefits associated with the pure neurotoxic component include a fast onset of effect and an excellent temperature stability, which even obviates the need for a cold chain and storage in a refrigerator. A formulation containing only the neurotoxic component of type A without any complexing proteins is commercially available from Merz under the trade name Xeomin® and Bocouture®.

The neurotoxic component can be prepared by cultivating *botulinum* toxin producing clostridial strains and isolating the neurotoxic component from the produced *botulinum* toxin complex through a series of precipitation and chromatographic steps. If naturally occurring clostridial strains are used, the *botulinum* toxin is produced and released by clostridial bacteria in its active, acutely toxic form. Therefore, specific measures must be taken to avoid unfavorable health consequences to the personnel concerned with the production of the *botulinum* toxin and/or the purification of the neurotoxic component from the toxin complex. In order to reduce the risk of exposure to toxic aerosols, WO 2006/133818 A1 proposes, for example, to conduct the production of *botulinum* toxins in an isolator operated at a lower pressure than that of the surrounding production room to avoid contact of the operator with any toxic material.

While the manufacturing process described in WO 2006/133818 A1 ensures adequate operational safety, it still leaves room for improvements in the purity of the neurotoxic component produced. In the pharmaceutical industry, a high chemical and microbial purity is critically important. Therefore, the ultimate goal of drug developers is to achieve drug purity as high as possible to establish the desired safety and efficacy.

Accordingly, the objective of the present invention is to provide an improved process for preparing a highly pure neurotoxic component of a *botulinum* toxin in a safe manner.

SUMMARY OF THE INVENTION

In a first aspect, the present invention provides a process for preparing a highly pure neurotoxic component of a *botulinum* toxin, the process comprising the steps of:

(a) cultivating *Clostridium botulinum* under conditions that allow production of a *botulinum* toxin, and (b) isolating the neurotoxic component from the *botulinum* toxin, wherein cultivating step (a) and isolating step (b) are conducted in a pressure gradient device, which comprises a first isolator unit containing a fermenter for cultivating *Clostridium botulinum* and, optionally, a second or further isolator unit as well as a safety work bench which is a Class II BSC (Biological Safety Cabinet) provided with a transfer system that allows for the aseptic transfer of material into and out of the BSC.

The first and second or further isolator units are located in a production room that is connected to the environment via an air lock, wherein the pressure in the first and second or further isolator units is lower than that in the production room, the pressure in the production room is lower than ambient pressure, and the pressure in the air lock is higher than ambient pressure. The safety work bench is also located in the production room.

In another aspect, the present invention provides a highly pure neurotoxic component of a *Clostridium botulinum* toxin having a single-chain content of less than 2.00 wt. %.

In yet another aspect, the present invention provides a pharmaceutical composition comprising a highly pure neurotoxic component of a *Clostridium botulinum* toxin as described herein and one or more pharmaceutically acceptable carriers.

In a yet further aspect, the present invention provides a highly pure neurotoxic component of a *Clostridium botulinum* toxin as described herein for use as a medicament.

In still another aspect, the present invention provides a highly pure neurotoxic component of a *Clostridium botulinum* toxin as described herein for use in the treatment of a disease associated with hyperactive cholinergic innervation of muscles or exocrine glands.

Preferred embodiments of the present invention are set forth in the appended dependent claims.

DETAILED DESCRIPTION OF A PREFERRED EMBODIMENT

It has been surprisingly found that there are key production parameters that have not been considered so far but which can exert a profound influence upon the quality, in particular upon the purity, of a neurotoxic component of a *botulinum* toxin. Furthermore, the production process of the present invention meets the legal requirements pertaining to safety, health and the environment, and fosters a safe and non-hazardous work environment. In other words, the present invention is based on the unexpected finding that additional modes of operation of the manufacturing process exist, which are not only safe with respect to environmental and human health issues but also provide a neurotoxic component of a *botulinum* toxin of superior quality, in particular superior quality.

In a first aspect, the present invention relates to a process for preparing a highly pure neurotoxic component of a *botulinum* toxin, the process comprising the steps of:

(a) cultivating *Clostridium botulinum* under conditions that allow production of a *botulinum* toxin, and (b) isolating the neurotoxic component from the *botulinum* toxin.

As used herein, the terms "*botulinum* toxin" or "*botulinum* toxin complex" are interchangeable and refer to a high molecular weight complex comprising the neurotoxic component of approximately 150 kDa and, in addition, non-toxic proteins of *Clostridium* spp., including hemagglutinin and non-hemagglutinin proteins. Also, the terms "*botulinum* toxin" and "*botulinum* toxin complex" are intended to cover all seven toxin serotypes (i.e. serotypes A, B, C, D, E, F and G) as well as subtypes thereof (e.g., A1, A2, C1, C2, etc.).

The term "neurotoxic component", as used herein, refers to the *botulinum* toxin protein molecule included in the *botulinum* toxin complex (also referred to as the "pure toxin" or the "pure neurotoxin"). In other words, a "neurotoxic component" within the meaning of the present invention is not associated with and devoid of any associated non-toxin proteins of *Clostridium botulinum*, including hemagglutinin and non-hemagglutinin proteins. Preferably, it is also free of RNA potentially associated with the neurotoxic component.

It is further pointed out that a "neurotoxic component" within the meaning of the present invention encompasses the single-chain precursor protein of approximately 150 kDa and the proteolytically processed di-chain form of the neurotoxic component, comprising the light chain (LC) of approximately 50 kDa and the heavy chain (HC) of approximately 100 kDa, which are commonly linked by one or more disulfide bonds. Those of skill in the art will appreciate that full biological activity is attained only after proteolytic activation, even though it is conceivable that the unprocessed precursor can exert some biological functions. "Biological function" may refer to (a) receptor binding, (b) internalization, (c) translocation across the endosomal membrane into the cytosol, and/or (d) endoproteolytic cleavage of proteins involved in synaptic vesicle membrane fusion.

Preferably, the neurotoxic component is derived from a naturally occurring *botulinum* toxin complex of serotype A, B, C, D, E, F or G. A particularly preferred neurotoxic component within the context of the present invention is derived from *Clostridium botulinum* toxin serotype A, in particular from the *Clostridium botulinum* toxin type A produced by the Hall strain (ATCC 3502). However, within the context of the present invention, a neurotoxic component may also be a recombinantly produced neurotoxic component, including a chimeric (fused) neurotoxic component. Also included are genetically modified neurotoxic components containing 1, 2, 3, 4, 5, 6, 7, 8, 9, 10 or up to 20 amino acid mutations. A mutation may be a substitution, an insertion or a deletion. In addition, neurotoxic components which contain chemically modified amino acids, for example one or more amino acids that are glycosylated, acetylated, lipidated or otherwise modified, are also comprised within the term "neurotoxic component".

The term "highly pure neurotoxic component" within the meaning of the present invention refers to a purified neurotoxic component, or a composition, preparation or formulation thereof, which essentially contains no other solid ingredients, and which may be prepared by the process described in detail herein. Furthermore, the term "highly pure", as used herein, refers to a neurotoxic component of a *botulinum* toxin, or a formulation, preparation or composition thereof that is free of complexing proteins (product-related impurities), other clostridial proteins (non-product related impurities), and non-clostridial proteins. Preferably, the term "highly pure" refers to a total purity of at least 99.90 wt. %, more preferably at least 99.95 wt. %, and most preferably at least 99.99 wt. %. "Total purity" means the weight percentage of the single-chain and two-chain forms of a neurotoxic component, based on the total weight of a sample of the highly pure neurotoxic component of the present invention. In accordance with the present invention, the purity is assessed by sodium dodecyl sulfate polyacrylamide gel electrophoresis (SDS-PAGE).

In step (a), *Clostridium botulinum* is cultivated (or fermented) in a suitable fermentation medium, such as a medium containing 2% proteose peptone, 1% yeast extract, 1% glucose and 0.05% sodium thioglycolate, in order to produce a *botulinum* toxin. As used herein, the term "cultivating" is interchangeably used with the term "fermenting". The term "*Clostridium botulinum*" is intended to include *Clostridium botulinum* type A, B, C, D, E, F or G. Within the context of the present invention, a *Clostridium botulinum* strain producing a *botulinum* toxin of type A, i.e. a *Clostridium botulinum* type A, is preferably used. Particularly preferred for use herein is *Clostridium botulinum* type A Hall strain (ATCC 3502) (in the following referred to as "the Hall strain"). Processes for cultivating *Clostridium botulinum* to produce the toxin complex are known in the art (see, e.g., Schantz E. and Kautter D., J. Assoc. Off. Anal. Chem. 61:96-99, 1978).

The fermentation (cultivation) temperature in step (a) of the process of the present invention depends on the specific *Clostridium botulinum* strain and fermentation conditions used. Preferably, the temperature is constantly maintained in a pre-defined, narrow temperature range. For example, for the production of *Clostridium botulinum* toxin type A, in particular the Hall strain, the fermentation temperature is preferably set to and maintained at 33.5° C.±1.0° C., more preferably 33.5° C.±0.5° C., and most preferably 33.5° C.±0.2° C.

It was found by the present inventors that a constant temperature of about 33.5° C. is the optimal temperature for *botulinum* toxin production. Temperatures that are too high, too low and/or too variable will cause the *Clostridium botulinum* to produce undesirable compounds. Surprisingly, it was found that, if the fermentation temperature is not controlled to be within the temperature ranges indicated above, the amount of the unwanted inactive single-chain form of the neurotoxic component significantly increases. It is stressed that, within the context of the present invention, the single-chain form of the neurotoxic component is regarded as being an undesirable "impurity" since it is not proteolytically processed and essentially inactive.

In line with the present invention, the fermentation temperature is preferably set to and maintained at the indicated temperature range using a heating jacket. As used herein, a "heating jacket" is a material that surrounds large surface areas, typically the entire side walls, of a fermenter and can be heated. For example, a heating jacket may incorporate different layers to provide the temperature stability required for the fermentation, such as a thermoelectric base layer for heating, an insulation layer to avoid temperature loss, and a waterproof outer layer for protection of the heating jacket from the hazards of the fermentation environment. In contrast to increasing and maintaining the temperature by means of a heating rod, the use of a heating jacket essentially avoids heating differences among different sites in the culture medium, even if the culture medium is not stirred as is typically the case for the process of the present invention, thereby ensuring a uniform temperature distribution.

The growth of the clostridial cultures during fermentation (i.e. the cell density) is preferably assessed by the turbidity of the culture, which may be suitably monitored by an on-line optical probe. The term "turbidity", as used herein, refers to the optical property that causes light to be scattered and absorbed rather than transmitted in straight lines through the sample. Turbidity can be measured by commercially available turbidimeters. These turbidimeters usually measure the amount of light scattered at right angles to an incident light beam by particles present in a fluid sample. In the present case, a turbidimeter is used to measure the light scattered by bacterial cells present in the culture medium at an angle of 90° relative to the incident light beam. In order to measure the cell density, which is defined herein as the number of *Clostridium botulinum* cells per unit volume of culture, the turbidimeter is calibrated with commercially available certified Formazin Turbidity Standards (i.e. defined particle suspensions). The measured turbidity values are expressed herein as Formazin Turbidity Units (FTU).

In the context of the present invention, the fermentation is generally continued until the cell density of the culture, after it has been increased due to bacterial growth, decreases due to cell lysis. For *Clostridium botulinum* type A, in particular for the Hall strain, the cell density after 24 hours of cultivation is preferably about 1.3±0.3 FTU. The pH after 24 hours is preferably about 5.7±0.2. At the end of the fermentation with *Clostridium botulinum* type A, in particular with the Hall strain, the cell density is preferably below 0.8 FTU. The pH at the end of the fermentation is usually about 5.5±0.3.

The fermentation time is, again for *Clostridium botulinum* type A and, in particular, for the Hall strain, typically in the range of from 65 to 80 hours and is, preferably, approximately 72 hours, e.g. 72 hours±4 hours, 72 hours±2 hours, 72 hours±1 hour or 72 hours±0.5 hours. The culture volume is not particularly limited but is typically in the range of about 10 to 40 liters, preferably about 20 liters. The yield of the *botulinum* toxin complex after fermentation using a *Clostridium botulinum* type A strain, in particular the Hall strain, is usually in the range of 3.5±2.0 µg, in particular 3.5±1.0 µg, based on 1 ml of the fermentation medium at the end of the fermentation.

Turbidity measurements, unlike transmitted light measurements that are conventionally used in the art for determining cell densities in fermentation broths, are not device-specific and give more accurate and, in particular, much better reproducible and comparable measurement results. Unexpectedly, it was found that the assessment of the cell density by turbidity measurements is not only highly accurate and repeatable, but also allows one to control the process so that formation of the single-chain form of the neurotoxic component is limited. Thus, the use of turbidity measurements for monitoring cell growth and, in particular, for determining the end point of the fermentation, makes it possible to decrease the amount of the unwanted single-chain form in the end product. This is a significant process improvement since current purification methods are not capable of separating the inactive (non-cleaved) single-chain form from the active (cleaved) two-chain form.

In accordance with the present invention, the *Clostridium botulinum* culture of step (a) is preferably obtained by (i) providing an initial culture of *Clostridium botulinum* having a cell density of 530 to 850 FTU, particularly 600 to 800 FTU, more particularly 650 to 750 FTU, and (ii) adding a pre-determined amount of the initial culture to a culture medium. Preferably, the initial culture is added to the fermentation medium in an amount of from 5.0% to 10.0% v/v, preferably in an amount of from 7.7% to 8.2% v/v. It is further preferred that the initial culture has an anaerobic viable count of at least $5.0 \times 10^5$ cfu/ml (colony-forming units/ml), particularly at least $2.0 \times 10^6$ cfu/ml, more particularly more than $1.0 \times 10^7$ cfu/ml, and most particularly from $1.0 \times 10^7$ cfu/ml to $1.0 \times 10^8$ cfu/ml. Within the present invention, the aerobic or anaerobic viable count is determined by plating dilution series of an initial sample on blood agar plates, incubating the plates at a given temperature (e.g., 37° C.) and for a given time (e.g., 40 hours to 72 hours) under aerobic or anaerobic conditions and counting the colonies grown, particularly according to Pharm. Eur. 2.6.12 and USP <61>.

The initial culture may be obtained, for example, by first preparing a pre-culture involving inoculation of a seed medium with *Clostridium botulinum* and growing the bacteria at a suitable growth temperature (e.g., 37° C.). An aliquot of the obtained pre-culture is then used for inoculation of a culture medium, followed by growing the bacteria at a suitable growth temperature. Next, an aliquot of the obtained pre-initial culture is used to inoculate a culture medium at a suitable growth temperature until the desired cell density is reached. Then, an aliquot of the obtained initial culture is used for inoculation of the fermentation medium used in step (a) of the process of the present invention.

The source of the *Clostridium botulinum* strain (e.g., the Hall strain) used within the present invention may be conveniently provided in form of a frozen aliquot of a working cell bank (WCB). The WCB is established from a master cell bank (MCB) of the respective strain according to techniques known in the art. The frozen aliquot of the WCB may, for example, be provided in the form of a cryovial containing 800 µl of the WCB and 200 µl sterile glycerol as cryoprotectant. Typically, the anaerobic viable count of the frozen aliquot of *Clostridium botulinum*, in particular the Hall strain, is at least $5.0 \times 10^5$ cfu/ml, preferably more than $1.0 \times 10^7$ cfu/ml. The frozen aliquots (e.g., cryovials) may be stored at −80° C. in a freezer or, preferably, at about −130° C. in the vapor phase of liquid nitrogen.

In step (b) of the process of the present invention, the neurotoxic component is isolated from the produced *botulinum* toxin (complex). Processes for purification of the neurotoxic component from toxin complexes produced by *Clostridium botulinum* are known in the art (see, e.g., DasGupta B. R. and Sathyamoorthy, V., Toxicon. 22:415-424, 1984; and WO 00/74703). The concentration of the purified neurotoxic component at the end of the purification is typically in the range of 100 µg/ml to 500 µg/ml, based on one ml of the final solution of the purified neurotoxic component.

A suitable isolation process for use within the present invention, in particular for the isolation of the neurotoxic component of *Clostridium botulinum* toxin type A, including the Hall strain, includes the step of acid precipitation of the *botulinum* toxin at the end of the fermentation (e.g., by adding 3 N sulfuric acid; final pH of about 3.5). After centrifugation, the precipitate is extracted (e.g., with 0.2 M sodium phosphate buffer, pH 6.0) to release the toxin complex into the solution. The extract is then subjected to protamine sulfate precipitation (e.g., 2% protamine sulfate) to precipitate nucleic acids from the supernatant, and the toxin complex is precipitated from the supernatant using ammonium sulfate (e.g., by adding 38 g ammonium sulfate per 100 g of supernatant).

After solubilization with phosphate buffer (e.g., 50 mM sodium phosphate, pH 6.0), the toxin is further purified by three ion exchange chromatographic steps in the following order: DEAE Sepharose Fast Flow, Q Sepharose Fast Flow and SP Sepharose Fast Flow. Following addition of glycerol, the final eluate is filtered through a sterile filter, such as a 0.22 µm filter to obtain the final product. This final product after purification can then be further processed, e.g. supplemented with stabilizing aids (e.g., human serum albumin (HSA) or sucrose) and/or lyophilized.

In accordance with the present invention, the cultivating step (a) and the isolating step (b) of the process of the present invention are conducted in a pressure gradient device. This device comprises a first isolator unit and, optionally, a second or further isolator unit, as well as a safety work bench. The safety work bench is used for aseptically loading the first isolator unit and/or second or further isolator unit with materials, in particular heat-sensitive materials which cannot be autoclaved (e.g., working cell banks). To this end, the material may be transferred from the safety work bench to the isolator(s) using a specific transfer system (e.g. an alpha/beta-port system available from the Getinge Group) as further described below. This is an important aspect of the present invention since it was found to result in less contamination (microbial and particular impurities) and higher purity of the neurotoxic component of a *botulinum* toxin.

Within the present invention, the safety work bench is a Class II BSC provided with a transfer system that allows for the aseptic transfer of material into and out of the BSC. A "biological safety cabinet" or "biosafety cabinet" or "BSC" within the meaning of the present invention is an enclosed, ventilated laboratory workspace for protecting the laboratory worker and the surrounding environment from risks of hazardous agents, such as bacteria, viruses or any other toxic or pathogenic agents, and for maintaining the sterility of materials inside the workspace. In other words, BSCs provide protection of experiment from ambient environment, and protection of ambient environment, from experiment. Within the context of the present invention, this also includes the transfer of heat-sensitive material into isolator 1 or isolator 2 without a sterilization step, e.g. cell banks.

Preferably, the BSC used for the safety work bench is a Class II BSC, more preferably a Class II, Type A1 or Type A2 BSC, most preferably a Class II, Type A2 BSC, as classified by the U.S. Centers for Disease Control and Prevention (CDC) (see U.S. Department of Health and Human Services, Public Health Service; Centers for Disease Control and Prevention; National Institutes of Health. *Biosafety in Microbiological and Biomedical Laboratories. Appendix A—Primary Containment for Biohazards: Selection, Installation and Use of Biological Safety Cabinets*. 5th Edition, HHS Publication No. (CDC) 21-1112, Revised December 2009) and defined by NSF/ANSI Standard 49-2007 (see NSF International (NSF); American National Standards Institute (ANSI). *NSF/ANSI Standard 49-2007. Class II (laminar flow) biosafety cabinetry*. Ann Arbor (Mich.); 2004). The safety work bench is typically operated at the same pressure as that of the production room.

A BSC comprises a work chamber, air supply means for supplying air of a unidirectional airflow traveling from an upper part to a lower part in the work chamber, and air discharge means for discharging air of the unidirectional airflow. Biosafety cabinets work by drawing a curtain of sterile air over the products that are being handled. The air is then drawn underneath the work surface (e.g., table or bench), back to the top. A part of the air is exhausted, while another part is again introduced into the working space to draw a curtain of sterile air. At some point in the system, the air passes through one or more filters, usually a HEPA (class of high efficiency particulate air) filter, so that both the exhaust air and the recirculation air are sterile and particle-free. The exhaust air is made up by air that is drawn into the front of the cabinet and then underneath the work surface to combine with the recirculation air drawn from the cabinet inside underneath the work surface. In case of a typical Class II, Type A1 BSC, approximately 30% of the air passes through an exhaust HEPA filter and approximately 70% recirculates through the supply HEPA filter back into the work zone of the cabinet. A Class II, Type A2 BSC is similar to the A1 Type, but the minimum inflow velocity is typically about 100 ft/min or more.

It should be understood that a "BSC" within the meaning of the present invention is not a "clean bench". A "clean bench", as used herein, refers to a horizontal laminar flow "clean bench" or vertical flow "clean bench", which generally only provide a Class 100 work area for procedures requiring a particle-free environment. The make-up air is filtered, while the exhaust air is not filtered. In contrast, both the make-up and exhaust air is filtered, e.g. HEPA-filtered, in case of BSCs. Thus, a clean bench does only provide product protection but does not prevent the worker from being exposed to materials being manipulated on the clean bench. Generally, clean benches are inappropriate for use with any potentially biohazardous materials, including toxic, mutagenic or carcinogenic substances, biological toxins, infectious agents (e.g., bacteria, viruses, parasites, etc.), and are generally not usable if aseptic conditions are required for the work.

The transfer system of the safety work bench preferably comprises a first transfer unit and a second transfer unit detachably connectable to each other, wherein the first transfer unit is a sealable part mounted on a surface of the BSC, usually fixed to a wall of the BSC, and the second transfer unit is a sealable container. The sealable container may be made of various materials, such as stainless steel, polyethylene and the like. It may be rigid or flexible, e.g. in form of a bag, and may be a single-use or reusable container. Preferably, the transfer system is the DPTE® transfer system (Getinge) comprised of two separate units, i.e. the Alpha and Beta parts, which are each fitted with a door, a lock and a sealing function and permit the successive transfer of materials without breaching integrity of the sterile or toxic environment contained within the Alpha or Beta component.

The pressure gradient device of the present invention further comprises a first isolator unit and, optionally, a second or further isolator unit. The first isolator unit and the second or further isolator unit are Class II BSCs provided with a transfer system that allows for the aseptic transfer of material into and out of the BSC. Generally, gloves are attached to the front to prevent contact with the neurotoxin. The transfer system may be, for example, the DPTE system described above in connection with the safety work bench. The first isolator unit contains a fermenter in which the step of cultivating *Clostridium botulinum* is conducted. Both the first and second or further isolator units are located in the production room that is connected to the environment via an air lock, wherein a pressure gradient is formed between the isolator unit(s), the production room and the air lock.

Specifically, the pressure in the first and second or further isolator units is lower than that in the production room, for example 10 to 100 Pa, preferably 20 to 80 Pa, more preferably 50 to 70 Pa, most preferably 60 Pa lower than in the production room. Furthermore, while the pressure in the production room is higher than that in the first and second or further isolator units, it is still lower than ambient pressure, for example 5 to 50 Pa, preferably 10 to 30 Pa, more preferably 12 to 18 Pa, and most preferably about 15 Pa lower than ambient pressure.

The pressure in the air lock is higher than ambient pressure, for example 10 to 100 Pa, preferably 20 to 80 Pa, more preferably 25 to 35 Pa, and most preferably 30 Pa higher than ambient pressure. In other words, there is typically a pressure difference between the air lock and the production room of about 15 to 150 Pa, preferably about 30 to 110 Pa, more preferably about 37 Pa to 53 Pa, and most preferably about 45 Pa. The term "ambient pressure" means the pressure of the surrounding atmosphere and is generally about 1 atmosphere, but may vary depending on geographical position or meteorological conditions.

The second or further isolator unit may be a BSC as that described above in relation to the first isolator unit. It may be operated at the same or different pressure as the first isolator unit. Furthermore, the first isolator unit may not or may be connected with the second or further isolator units by, for example, one or more lockable air locks, double trap container or ports. In accordance with the present invention, the cultivating step (a) and the isolating step (b) may be conducted in the first isolator unit. Preferably, however, the cultivating step and at least one stage of the purification step is conducted in the first isolator unit, whereas the remaining purification stages are carried out in the second or further isolator units. The first isolator unit may be operated at a higher temperature, e.g. at about 15° C. to 50° C. or 20° C. to 40° C., and the second or further isolator unit may be operated at a lower temperature, for example in the range of about −5° C. to +25° C. The term "about", as used in the context of the present invention, means "approximately" or "nearly". In the context of numerical values, without committing to a strict numerical definition, the term may be construed to estimate a value that is +/−10% of the value or range indicated.

The production room of the present invention is sealed and airtight room of that can be operated at negative pressure. It can be accessed from the outside by one or more air locks. The production room contains the safety work bench as well as the first isolator and, optionally, the second or further isolator. The supply of air into and out of the production room occurs preferably via filters, in particular HEPA filters. Inside the production room, there is a controlled temperature of, for example, 19° C. to 26° C., and a controlled relative humidity of, for example, 40% to 60%, particularly 55%. Certain operations or activities, including measurements or tests, which are necessary for or related to the production of the *botulinum* toxin may be executed outside an isolator unit, in particular if they are not associated with aerosol formation or if the biological active material is present in a form which does not pose any hazards for the persons engaged with *botulinum* toxin production.

In another aspect, the present invention relates to a highly pure neurotoxic component of a *Clostridium botulinum* toxin having a single-chain content of less than 2.00 wt. %. Preferably, the single-chain content is less than 1.90 wt. %, 1.80 wt. %, 1.70 wt. %, 1.60 wt. %, 1.50 wt. %, 1.40 wt. %, 1.30 wt. %, 1.20 wt. %, 1.10 wt. %, 1.00 wt. %, 0.90 wt. % or less than 0.80 wt. %. Furthermore, the highly pure neurotoxic component of the present invention has preferably a total purity of at least 99.90 wt. %, more preferably of at least 99.95 wt. %, and most preferably of 99.99 wt. %, wherein the term "total purity" has the meaning as defined above. In addition, the highly pure neurotoxic component of a *Clostridium botulinum* toxin of the present invention may have an endotoxin content of equal to or less than 5.0 IU, in particular equal to or less than 1.0 IU/ml, per ml of the final product after purification, i.e. typically one ml of a solution containing the highly pure neurotoxic component of a *botulinum* toxin in a concentration of 100 µg/ml to 500 µg/ml.

Furthermore, the highly pure neurotoxic component of a *Clostridium botulinum* toxin of the present invention has preferably a total aerobic viable cell count of less than 1 cfu/ml, preferably less than 0.5 cfu/ml, more preferably 0 cfu/ml, based on one ml of a solution containing the highly pure neurotoxic component of *botulinum* toxin in a concentration of 100 µg/ml to 500 µg/ml.

Moreover, the highly pure neurotoxic component of a *Clostridium botulinum* toxin of the present invention has a biological activity (relative potency) in an $LD_{50}$ assay of 4.0 to 8.0 µg protein/$LD_{50}$ unit, particularly 5.0 to 6.0 µg protein/$LD_{50}$ unit. The $LD_{50}$ assay used herein for the assessment of the biological activity is known in the art and described, for example, in Pearce L. B., Borodic G. E., First E. R., and MacCallum R. D., *Measurement of botulinum toxin activity: evaluation of the lethality assay*, Toxicol. Appl. Pharmacol. 128:69-77, 1994. The biological activity is expressed in "units" (U), wherein 1 U is defined as being the equivalent amount of toxin (i.e. the neurotoxic component) that kills 50% of a specified mouse population after intraperitoneal injection.

The above described highly pure neurotoxic component of a *Clostridium botulinum* toxin can be obtained by the process according to the invention. Thus, in a preferred embodiment of the present invention, the highly pure neurotoxic component of a *Clostridium botulinum* toxin described herein is prepared by the process according to the invention.

In a further aspect, the present invention relates to a pharmaceutical composition comprising a highly pure neurotoxic component of a *Clostridium botulinum* toxin and one or more pharmaceutically acceptable carriers. A "pharmaceutical composition" is a formulation in which an active ingredient is contained or comprised. The dosage form of the pharmaceutical composition is not particularly limited but is preferably a parenteral formulation, such as an aqueous or non-aqueous solution or dispersion for injection or infusion. The pharmaceutical composition of the present invention may be lyophilized or vacuum dried, reconstituted or in solution. When reconstituted, it is preferred that the reconstituted solution is prepared by adding sterile physiological saline (i.e., 0.9 wt. % NaCl).

The pharmaceutical composition generally includes an effective amount of the neurotoxic component of the present invention. Within the present invention, the term "effective amount" refers to an amount of neurotoxic component which, after administration, results in a partial or complete removal of disease symptoms or conditions. A therapeutically effective amount can be administered in one or more administrations, applications or dosages and is not intended to be limited to a particular formulation or administration route. Effective amounts are generally in the range of 1 to 2000 U. However, also doses of up to 5000 U may be used. When high doses of the neurotoxic component are to be administered to a subject, it may be beneficial to split the treatment into more than one treatment session. The term "more than one treatment session" means, e.g., 2, 3, 4, 5, 6, 7, 8, 9 or 10 treatment sessions.

Within the context of the present invention, a "carrier" refers to a diluent or vehicle whereby the active ingredient is administered. Suitable carriers for use herein include sterile liquids or dispersions, especially those suited for parenteral administration (e.g., by intramuscular or subcutaneous injection), as discussed in Remington: The Science and Practice of Pharmacy, 20th Edition (2000). Preferably, the carrier is water or an aqueous pH buffer, such as a phosphate buffer, phosphate buffered saline (PBS) or an acetate buffer. The term "pharmaceutically acceptable", as used herein, refers to those compounds or substances which are, within the scope of sound medical judgment, suitable for contact with the tissues of mammals, especially humans, without excessive toxicity, irritation, allergic response and other problem complications.

In addition, the pharmaceutical composition of the present invention may include additional components, such as excipients, stabilizers and/or cryoprotectants. The excipients may include, but are not limited to, sugars (e.g., mono- or disaccharides like sucrose), salts (e.g., NaCl), detergents (e.g., non-ionic, anionic or cationic surfactants), and chelating agents (e.g., EDTA). Examples of stabilizers include proteinaceous stabilizers, for example gelatin or albumin (i.e. HSA), and non-proteinaceous stabilizers, for example hyaluronic acid, polyvinylpyrrolidone, polyethyleneglycol and mixtures thereof. The cryoprotectants exert a stabilizing effect on proteins (i.e. the neurotoxic component) during lyophilization and include, inter alia, alcohols, especially polyalcohols like inositol, mannitol or glycerol. Also, the pharmaceutical composition may include one or more additional active substances that are co-administered with the neurotoxic component of the present invention.

Preferably, the pharmaceutical composition of the present invention comprises a highly pure neurotoxic component as described herein, a pH buffer, preferably a phosphate buffer or an acetate buffer, and a hyaluronic acid stabilizer or a polyvinylpyrrolidone stabilizer or a polyethyleneglycol stabilizer or a BSA or HSA stabilizer. Additionally, the pharmaceutical composition may comprise a polyalcohol and/or a detergent.

In yet a further aspect, the present invention relates to the use of a neurotoxic component of a *Clostridium botulinum* toxin of the present invention as a medicament. A "medicament", as used herein, refers to any composition comprising a neurotoxic component of a *Clostridium botulinum* toxin for the treatment of a disease. In this context, the term "disease" is not limited to a particular disease, but includes any disorder or condition that disrupts body functions, systems or organs.

In still another aspect, the present invention relates to the use of a neurotoxic component of a *Clostridium botulinum* toxin of the present invention for the treatment of a disease or condition associated with hyperactive cholinergic innervation of muscles or exocrine glands. The term "treatment", as used herein, includes therapeutic treatment and prophylactic treatment (prevention) as well as cosmetic treatment of a disease or condition. A "treatment" within the meaning of the present invention generally involves the administration of an effective amount of highly pure *Clostridium botulinum* neurotoxic component of the present invention to a subject having the disease or condition associated with hyperactive cholinergic innervation of muscles or exocrine glands.

The term "subject", as used herein, refers to a mammal, preferably a human. The subject may have never been exposed to *botulinum* toxin, or may have been exposed to *botulinum* toxin. The term "effective amount", as used in this context, has the same meaning as described above in connection with the pharmaceutical composition.

The term "hyperactive cholinergic innervation", as used herein, relates to a synapse, which is characterized by an unusually high amount of acetylcholine release into the synaptic cleft. "Unusually high" relates to an increase of up to 25%, up to 50% or more with respect to a reference activity which may be obtained, for example, by comparing the release with the release at a synapse of the same type, but which is not in a hyperactive state, wherein muscle dystonia may be indicative of the hyperactive state. "Up to 25%"

means, for example, about 1% to about 25%. Methods for performing the required measurements are known in the art.

Exemplary diseases or conditions associated with hyperactive cholinergic innervation of muscles or exocrine glands are described in detail in Dressler, D., *Botulinum Toxin Therapy*, Thieme, Stuttgart, N.Y., 2000, and include, but are not limited to, dystonia (e.g., cranial dystonia, cervical dystonia, pharyngeal dystonia, laryngeal dystonia, limb dystonia), cosmetic use (e.g., craw's feet, frowning, facial asymmetries, mentalis dimples), strabism, exocrine gland hyperactivity (e.g., Frey syndrome, Crocodile Tears syndrome, hyperhidrosis), rhinorrhea, hypersalivation (drooling), spastic conditions, and other diseases.

Other diseases associated with hyperactive cholinergic innervation of muscles or exocrine glands include, for example, palatal myoclonus, myoclonus, myokymia, rigidity, benign muscle cramps, hereditary chin trembling, paradoxic jaw muscle activity, hemimasticatory spasms, hypertrophic branchial myopathy, maseteric hypertrophy, tibialis anterior hypertrophy, nystagmus, oscillopsia, supranuclear gaze palsy, epilepsia partialis continua, planning of spasmodic torticollis operation, abductor vocal cord paralysis, recalcitrant mutational dysphonia, upper oesophageal sphincter dysfunction, vocal fold granuloma, stuttering, Gilles de la Tourette syndrome, middle ear myoclonus, protective larynx closure, postlaryngectomy speech failure, protective ptosis, entropion, sphincter Odii dysfunction, pseudoachalasia, nonachalsia oesophageal motor disorders, vaginismus, postoperative immobilization, tremor, bladder dysfunction, hemifacial spasm, reinnervation dyskinesias, stiff person syndrome, tetanus, prostate hyperplasia, adipositas treatment, infantile cerebral palsy, achalasia and anal fissures.

Suitable administration routes include, but are not limited to, parenteral administration, in particular subcutaneous and intramuscular injection. The administration regimen is not particularly limited and includes, for example, bi-weekly, monthly, once every other month, once every third, sixth or ninth month and once-a-year or single application administration schemes. The therapeutically effective dose of the highly pure neurotoxic component of the present invention that is administered to the subject depends on the mode of application, the type of disease or condition, the subject's weight, age, sex and state of health, and the like. Administration can be single or multiple, as required. The highly pure neurotoxic component of the present invention may also be co-administered with other active substances.

The present invention will now be further illustrated by the following, non-limiting examples.

EXAMPLES

The following examples show that the use of a pressure gradient device as described herein permits the creation of working zones that are aseptic and have an extremely low number of airborne particles. This has surprisingly been found to have a strong impact on the overall product quality, in particular with respect to purity of the neurotoxic component.

Example 1

Construction of a Safety Work Bench

The "Alpha" part of a DPTE® transfer system (Getinge Group) was mounted on the right side wall of a HERAsafe® (NSF) Class II, Type A2 biological safety cabinet equipped with HEPA filters (Thermo Fisher Scientific, Inc.). A rigid transfer container (DPTE 190 Beta container made of stainless steel) was used as the movable DPTE® "Beta" part. The two separate units of the DPTE® transfer system, i.e. the Alpha and Beta parts, are each fitted with a door, a lock and a sealing function and permit the successive transfer of toxic or pathogenic materials without breaching integrity of the sterile or toxic environment contained within the Alpha or Beta component.

In all experiments described below, this safety workbench was used and located in a production room (operated at neutral pressure relative to that of the production room). The production room was operated at a temperature of 19° C. to 26° C. and a pressure of −15 Pa relative to ambient pressure. In the production room, there were further two isolators (isolator 1: fermentation; isolator 2: purification) operated at a pressure of −60 Pa relative to the pressure in the production room. The production room was connected to the environment by a personnel air lock and a material air lock.

Example 2

Microbial Purity in the Isolator Unit of the Present Invention

The aim of this study was to show that cultivation of *Clostridium botulinum* using the process of the invention is carried out under aseptic conditions. Therefore all cultivation procedures were simulated without microorganisms in three consecutive runs. All culture media and additives were replaced by media for sterility testing (TSB- and thioglycolate medium for aerob or anaerob process conditions).

To verify the absence of microbiological contamination, samples taken from the different process steps were incubated for at least 14 days, but not exceeding 21 days, at 20° C. to 35° C. as follows: incubation at 20° C. to 25° C. for at least 7 days, directly followed by incubation at 30° C. to 35° C. for at least 7 days.

As can be seen from Table 1, no microbial contaminations could be detected throughout the different cultivation stages. This demonstrates that the isolator used within the present invention—despite being operated at lower pressure than that of the production room, which results in the influx of potential impurities—allows for aseptic process control.

TABLE 1

Microbial contamination in the isolator unit

| Process stage of fermentation | Experiment 1 (aerob) | Experiment 2 (aerob) | Experiment 3 (anaerob) |
|---|---|---|---|
| | | Microbial contaminations | |
| Preculture | none | none | none |
| Initial culture 1 | none | none | none |
| Glucose solution | none | none | none |
| Initial culture 2 | none | none | none |
| Fermentation culture 96 h | none | none | none |
| Fermentation culture 120 h | none | none | none |

In addition, the number of airborne germs was determined at three different measuring points (designated MP18, MP19 and MP20) in the isolator unit 1. As shown in Table 2, no airborne germs could be detected at all three measuring points. In contrast, the average number of airborne germs in the production room, as measured in 2010, was found to be 3 cfu/m$^3$.

TABLE 2

Number of airborne germs in the isolator unit

| | Measuring point in the isolator unit | | | | | |
|---|---|---|---|---|---|---|
| | MP18 | MP19 | MP20 | MP18 | MP19 | MP20 |
| Lot. | Airborne germs [cfu/m³] | | | | | |
| MP050807 | 0 | 0 | 0 | | | |
| | | | | 0 | 0 | 0 |
| MP050908 | 0 | 0 | 0 | | | |
| | | | | 0 | 0 | 0 |
| MP051009 | 0 | 0 | 0 | | | |
| | | | | 0 | 0 | 0 |
| MP061201 | 0 | 0 | 0 | | | |
| | | | | 0 | 0 | 0 |
| MP071007 | 0 | 0 | 0 | | | |
| | | | | 0 | 0 | 0 |
| MP090201 | 0 | 0 | 0 | | | |
| | | | | 0 | 0 | 0 |
| MP091002 | 0 | 0 | 0 | | | |
| | | | | 0 | 0 | 0 |
| MP110504 | 0 | 0 | 0 | | | |
| | | | | 0 | 0 | 0 |

Thus, the use of an isolator unit as employed in the process of the present invention allows the creation of working zones that are free of microbial contamination and airborne germs.

Example 3

Particle Content in the Isolator Unit

Another important factor, in addition to microbial contamination and number of airborne germs, which determines product quality is the concentration of particulate impurities. This is of particular significance in the pharmaceutical industry, where the protection of a given product from (airborne) particles is critically important. Therefore, the number of airborne particles in different working zones (designated MP18, MP19, and MP20) of the isolator unit used within the present invention was measured. The particle measurement was conducted by using a particle counter commercially available from CAS Clean-Air-Service AG, Switzerland. The results are shown in Table 3 below.

TABLE 3

Number of airborne particles

| | Particles ≥0.5 µm [ft⁻³] | | | Particles ≥5.0 µm [ft⁻³] | | |
|---|---|---|---|---|---|---|
| | Measuring point in the isolator | | | | | |
| Lot No. | MP18 | MP19 | MP20 | MP18 | MP19 | MP20 |
| MP050807 | 5 | 5 | 8 | 0 | 0 | 0 |
| | 3 | 15 | 18 | 1 | 1 | 1 |
| MP050908 | 5 | 2 | 7 | 3 | 1 | 2 |
| | 7 | 13 | 1 | 3 | 4 | 0 |
| MP051009 | 0 | 5 | 1 | 0 | 1 | 0 |
| | 10 | 6 | 3 | 1 | 2 | 0 |
| MP061201 | 1 | 2 | 3 | 0 | 0 | 1 |
| | 5 | 6 | 5 | 1 | 1 | 1 |
| MP071007 | 1 | 0 | 0 | 0 | 0 | 0 |
| | 2 | 14 | 3 | 1 | 0 | 2 |
| MP090201 | 0 | 5 | 0 | 0 | 3 | 0 |
| | 3 | 6 | 7 | 0 | 0 | 1 |
| MP091002 | 0 | 0 | 0 | 0 | 0 | 0 |
| | 0 | 11 | 3 | 0 | 2 | 1 |
| MP110504 | 2 | 1 | 2 | 0 | 0 | 0 |
| | 3 | 1 | 1 | 2 | 0 | 0 |

The results show that the isolator unit used within the present invention contains only very few particles with a diameter ≥0.5 µm and essentially no particles with a diameter ≥5.0 µm at all three measuring points. In contrast, the average particle numbers in the production room, as measured in 2010, was found to be 434 per ft³ for particles with diameters ≥0.5 µm, and 22 per ft³ for particles with diameters ≥5.0 µm. This demonstrates the very high particulate purity in the isolator unit of the present invention compared to that in the surrounding production room.

Example 4

Product Quality in Terms of Biochemical Purity

The total purity and single-chain content of different lots of neurotoxic components purified from *Clostridium botulinum* toxin type A produced by the Hall strain (ATCC 3502) with use and without use of the isolator of the present invention were determined.

A volume of 10 ml culture medium was inoculated with an aliquot of a Working Cell Bank of *Clostridium botulinum* type A Hall strain (ATCC 3502) to obtain a preculture of a total volume of 10 ml. An aliquot of the preculture was used to inoculate 50 ml medium to obtain Initial Culture 1. Initial Culture 2 was then obtained by inoculating 1600 ml medium with an aliquot of Initial Culture 1. The medium of the fermentation culture (17.4 l) was sterilized in situ in the fermenter. After adding 1 l of sterile glucose solution, the fermentation culture is inoculated with 1600 ml of Initial Culture 2. Fermentation was carried out at 33.5° C. for 72 h.

The purification was performed out as described hereinabove. "Total purity" is defined as the weight percentage of the single-chain and two-chain forms of the neurotoxic component, based on the total weight of a sample of the purified neurotoxic component. The results obtained are shown in Table 4 below.

TABLE 4

Total purity of the neurotoxic component of *Clostridium botulinum* toxin type A

| Prepared without isolator | | Prepared with isolator | |
|---|---|---|---|
| Lot No. | Total purity [%] | Lot. No. | Total purity [%] |
| A 29-02 | 98.8 | MP050403 | 100.0 |
| A 30-02 | 97.0 | MP050606 | 100.0 |
| A 31-02 | 97.6 | MP050807 | 100.0 |
| Mean value | 97.8 | MP050908 | 99.0 |
| | | MP051009 | 100.0 |
| | | MP101003 | 100.0 |
| | | MP110101 | 100.0 |
| | | MP110302 | 100.0 |
| | | Mean value | 99.9 |

As can be seen from Table 4, the total purity of the neurotoxic component prepared according to the present invention is as high as 99.9 wt. %. In comparison, the total purity obtained without using the isolator technology of the present invention is only 97.8 wt. %. In other words, the neurotoxic component formulation prepared according to the present invention consists essentially only of the neurotoxic component (in single-chain or two-chain form), whereas the neurotoxic component formulation prepared without using the isolator technology of the present invention contains a significant amount of contamination of 2.2 wt. %.

The lots of Table 4 were further evaluated with regard to their content of the single-chain form of the neurotoxic component. SDS-PAGE with photometric evaluation was used to determine the single-chain content. The single-chain content is an especially important parameter since the uncleaved single-chain form is essentially inactive and, thus, an "impurity" within the meaning of the present invention. Furthermore, it cannot be chromatographically resolved from the active two-chain form. The results are shown in Table 5.

TABLE 5

Content of the single-chain form of the neurotoxic component

| Prepared without isolator | | Prepared with isolator | |
| --- | --- | --- | --- |
| Lot No. | Single-chain content [wt. %] | Lot No. | Single-chain content [wt. %] |
| A 29-02 | 1.8 | MP050403 | 0.4 |
| A 30-02 | 1.9 | MP050606 | 0.8 |
| A 31-02 | 1.4 | MP050807 | 2.0 |
| Mean value | 1.7 | MP050908 | 1.3 |
| | | MP051009 | 1.1 |
| | | MP101003 | 1.6 |
| | | MP110101 | 1.3 |
| | | MP110302 | 1.2 |
| | | Mean value | 1.2 |

The results unexpectedly show that the process of the present invention provides a mean single-chain content of 1.2 wt. % compared to the 1.7 wt. % obtained for the comparative lots.

Example 5

Product Quality in Terms of Microbial Purity

The microbial purity (bioburden) of the product was assessed by measuring the aerobic microbial bioburden according to Pharm. Eur. 2.6.12 and USP <61> at different process stages of lots prepared according to the present invention in comparison to lots prepared without the isolator technology used in the present invention. The results are shown in Tables 6, 7, and 8.

TABLE 6

Aerobic bioburden at early process stage "after dialysis 1"

| Prepared without isolator | | Prepared with isolator | |
|---|---|---|---|
| Lot No. | Total aerobic count [cfu/ml] | Lot. No. | Total aerobic count [cfu/ml] |
| A 29-02 | 220 | MP050807 | <10 |
| A 30-02 | 440 | MP050908 | <10 |
| A 31-02 | 980 | MP051009 | <10 |
| Mean value | 547 | MP101003 | <5 |
| | | MP110101 | <5 |
| | | MP110302 | <5 |
| | | Mean value | <8 |

TABLE 7

Aerobic bioburden at late process stage "SP-Pool"

| Prepared without isolator | | Prepared with isolator | |
|---|---|---|---|
| Lot No. | Total aerobic count [cfu/ml] | Lot. No. | Total aerobic count [cfu/ml] |
| A 29-02 | 28 | MP050807 | <10 |
| A 30-02 | 52 | MP050908 | <10 |
| A 31-02 | 34 | MP051009 | <10 |
| Mean value | 38 | MP101003 | <5 |
| | | MP110101 | <5 |
| | | MP110302 | <5 |
| | | Mean value | <8 |

TABLE 8

Aerobic bioburden of the final product obtained at the end of the purification process

| Prepared without isolator | | Prepared with isolator | |
|---|---|---|---|
| Lot No. | Total aerobic count [cfu/ml][1] | Lot No. | Total aerobic count [cfu/ml][1] |
| A 29-02 | <2 | MP101003 | 0 |
| A 30-02 | <2 | MP110101 | 0 |
| A 31-02 | <2 | MP110302 | 0 |
| Mean value | <2 | Mean value | 0 |

[1]= based on one ml of the final product (solution containing 100-500 μg/ml highly purified neurotoxic component The results presented in Tables 6, 7 and 8 show that the bioburden at an early process stage (after dialysis 1) of the process according to the present invention is <8 and, thus, much lower than the mean value of 547 obtained without using an isolator of the present invention. This ensures that there is no aerobic (bacterial) count in the final product.

Example 6

Product Quality in Relation to Endotoxin Contamination

The endotoxin level of lots prepared according to the present invention was measured according to Pharm. Eur. 2.6.14 and USP <85> and compared with that determined for lots prepared without using the isolator technology of the present invention. The endotoxin values measured are indicated in IU per ml of the final product (solution containing 100-500 μg/ml of highly purified neurotoxic component). The results are shown in Table 9.

TABLE 9

Endotoxin load of the final product

| Prepared without isolator | | Prepared with isolator | |
|---|---|---|---|
| Lot No. | Endotoxin content [IU/ml] | Lot. No. | Endotoxin content [IU/ml] |
| A 29-02 | <2.0 | MP050403 | <1.0 |
| A 30-02 | <1.5 | MP050606 | <0.8 |
| A 31-02 | <1.5 | MP050807 | <0.8 |
| Mean value | <1.7 | MP050908 | <0.8 |
| | | MP051009 | <0.8 |
| | | MP101003 | <0.8 |
| | | MP110101 | <0.8 |
| | | MP110302 | <0.8 |
| | | Mean value | <0.8 |

As can be seen from Table 9, the endotoxin levels of lots prepared according to the present invention are significantly lower than that of the comparative lots. The mean endotoxin level of <0.8 IU/ml found for the inventive neurotoxic component is an acceptable endotoxin level for a *botulinum* toxin-containing pharmaceutical product.

The above results show that the process of the present invention allows for the preparation of a highly pure neurotoxic component of a *botulinum* toxin while at the same time meeting the standards on occupational health and safety.

The invention claimed is:

1. A highly pure neurotoxic component of a *Clostridium botulinum* toxin having a single-chain content of less than 2.00 wt. %, obtainable by a process comprising:
   (a) cultivating *Clostridium botulinum* under conditions that allow production of a *botulinum* toxin, and
   (b) isolating the neurotoxic component from the *botulinum* toxin,
   wherein cultivating (a) and isolating (b) are conducted in a pressure gradient device, the pressure gradient device comprising a first isolator unit containing a fermenter for cultivating *Clostridium botulinum* and a safety work bench, and optionally a second or further isolator unit, wherein the first and second or further isolator units are located in a production room that is connected to the environment via an air lock, the pressure in the first and second or further isolator units being lower than that in the production room, the pressure in the production room being lower than ambient pressure, and the pressure in the air lock being higher than ambient pressure, and wherein the safety work bench is located in the production room and is a Class II BSC (Biological Safety Cabinet) provided with a transfer system that allows for the aseptic transfer of material into and out of the BSC.

2. The highly pure neurotoxic component of claim 1, wherein cultivating temperature is maintained at a temperature of 33.5° C.±1.0° C.

3. The highly pure neurotoxic component of claim 1, wherein cell density during cultivating (a) is monitored by turbidity measurements using formazin as a primary turbidity standard.

4. The highly pure neurotoxic component of claim 1, wherein cultivating *Clostridium botulinum* is continued until cell density decreases from a cell density of 1.3±0.3 FTU reached after 24 hours of cultivation to less than 0.8 FTU.

5. The highly pure neurotoxic component of claim 1, wherein *Clostridium botulinum* culture used in (a) is obtained by (i) providing an initial culture of *Clostridium botulinum* having a cell density of 530 to 850 FTU and (ii) adding a pre-determined amount of initial culture to a fermentation medium.

6. The highly pure neurotoxic component of claim 5, wherein the initial culture is added to the fermentation medium in an amount of from 5.0% to 10.0% v/v.

7. The highly pure neurotoxic component of claim 1, wherein the transfer system of the Class II BSC comprises a first transfer unit and a second transfer unit detachably connectable to each other, the first transfer unit being a sealable part mounted on a surface, or fixed to a wall, of the BSC, and the second transfer unit being a sealable container.

8. The highly pure neurotoxic component of claim 1, wherein the *Clostridium botulinum* is *Clostridium botulinum* type A, including the Hall strain (ATCC 3502).

9. The highly pure neurotoxic component of claim 1, further having a total purity of at least 99.90 wt. %.

10. The highly pure neurotoxic component of claim 1, further having an endotoxin content of 5.0 IU/ml or less and/or a total anaerobic viable count of less than 1 cfu/ml.

11. A pharmaceutical composition comprising a highly pure neurotoxic component of a *Clostridium botulinum* toxin according to claim 1 and one or more pharmaceutically acceptable carriers.

12. A medicament comprising a highly pure neurotoxic component of a *Clostridium botulinum* toxin according to claim 1.

13. A method for treatment of a disease or condition associated with hyperactive cholinergic innervation of muscles or exocrine glands comprising employing a highly pure neurotoxic component of a *Clostridium botulinum* toxin according to claim 1.

14. A method of making the highly pure neurotoxic component of claim 1, comprising:
   (a) cultivating *Clostridium botulinum* under conditions that allow production of a *botulinum* toxin, and
   (b) isolating the neurotoxic component from the *botulinum* toxin,
   wherein cultivating (a) and isolating (b) are conducted in a pressure gradient device, the pressure gradient device comprising a first isolator unit containing a fermenter for cultivating *Clostridium botulinum* and a safety work bench, and optionally a second or further isolator unit, wherein the first and second or further isolator units are located in a production room that is connected to the environment via an air lock, the pressure in the first and second or further isolator units being lower than that in the production room, the pressure in the production room being lower than ambient pressure, and the pressure in the air lock being higher than ambient pressure, and wherein the safety work bench is located in the production room and is a Class II BSC (Biological Safety Cabinet) provided with a transfer system that allows for the aseptic transfer of material into and out of the BSC.

15. The method according to claim 14, wherein cultivating temperature is maintained at a temperature of 33.5° C.±1.0° C.

16. The method according to claim 14, wherein cell density during cultivating (a) is monitored by turbidity measurements using formazin as a primary turbidity standard.

17. The method according to claim 14, wherein cultivating *Clostridium botulinum* is continued until cell density decreases from a cell density of 1.3±0.3 FTU reached after 24 hours of cultivation to less than 0.8 FTU.

18. The method according to claim 14, further comprising in (a):
   (i) providing an initial culture of *Clostridium botulinum* having a cell density of 530 to 850 FTU and
   (ii) adding a pre-determined amount of initial culture to a fermentation medium.

19. The method according to claim 18, wherein initial culture is added to the fermentation medium in an amount of from 5.0% to 10.0% v/v.

20. The method according to claim 14, wherein the highly pure neurotoxic component of claim has a total purity of at least 99.90 wt. %.

* * * * *